(12) United States Patent
Markworth et al.

(10) Patent No.: US 7,811,311 B2
(45) Date of Patent: Oct. 12, 2010

(54) SCREW WITH DEPLOYABLE INTERLACED DUAL RODS

(75) Inventors: Aaron D. Markworth, Mountain View, CA (US); Hugues F. Malandain, Mountain View, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 800 days.

(21) Appl. No.: 11/027,501

(22) Filed: Dec. 30, 2004

(65) Prior Publication Data

US 2006/0149237 A1 Jul. 6, 2006

(51) Int. Cl.
*A61B 17/56* (2006.01)

(52) U.S. Cl. .................. 606/278; 606/250; 606/251; 606/256

(58) Field of Classification Search ............ 606/61, 606/60, 250–253, 256, 259, 260; 403/167, 403/169, 174, 175, 177, 178, 186, 217–219, 403/389, 391, 396, 399
See application file for complete search history.

(56) References Cited

U.S. PATENT DOCUMENTS

| | | | |
|---|---|---|---|
| 3,779,240 A | 12/1973 | Kondo | |
| 4,493,317 A | 1/1985 | Klaue | |
| 4,763,644 A | 8/1988 | Webb | |
| 4,805,602 A | 2/1989 | Puno et al. | |
| 4,946,458 A | 8/1990 | Harms et al. | |
| 5,005,562 A | 4/1991 | Cotrel | |
| 5,053,036 A | 10/1991 | Perren et al. | |
| 5,057,111 A | 10/1991 | Park | |
| 5,129,388 A | 7/1992 | Vignaud et al. | |
| 5,129,899 A | 7/1992 | Small et al. | |
| 5,147,361 A | 9/1992 | Ojima et al. | |
| 5,151,103 A | 9/1992 | Tepic et al. | |
| 5,171,279 A | 12/1992 | Mathews | |
| 5,176,678 A | 1/1993 | Tsou | |
| 5,176,679 A * | 1/1993 | Lin ............................. | 606/61 |
| 5,180,381 A | 1/1993 | Aust et al. | |
| 5,207,678 A | 5/1993 | Harms et al. | |
| 5,234,431 A | 8/1993 | Keller | |
| 5,246,442 A | 9/1993 | Ashman et al. | |
| 5,253,406 A | 10/1993 | Shere et al. | |
| 5,261,909 A | 11/1993 | Sutterlin et al. | |

(Continued)

FOREIGN PATENT DOCUMENTS

DE 94 02 695 U1 4/1994

(Continued)

*Primary Examiner*—Eduardo C Robert
*Assistant Examiner*—Tara R Carter

(57) ABSTRACT

A medical device and methods of use thereof are provided for supporting a structure (e.g., bone). A screw assembly is provided that is comprised of a base, one or more arms, and an interconnection means for coupling the base to the one or more arms. The interconnection means allows the arm to be positionable in a first position that is parallel to a long axis of the base and positionable in a second position that is perpendicular to the long axis of the base. The base is configured for attachment to a structure and the one or more arms configured for attachment to one or more support structures. A support structure is provided that includes an aperture having locking means, which can be configured as an open-ended saddle for attachment to a medical device (e.g., a screw assembly) after installation in a patient.

20 Claims, 8 Drawing Sheets

U.S. PATENT DOCUMENTS

| | | | |
|---|---|---|---|
| 5,269,784 A | 12/1993 | Mast | |
| 5,290,288 A | 3/1994 | Vignaud et al. | |
| 5,324,290 A | 6/1994 | Zdeblick et al. | |
| 5,360,431 A | 11/1994 | Puno et al. | |
| 5,395,371 A | 3/1995 | Miller et al. | |
| 5,429,639 A | 7/1995 | Judet | |
| 5,443,467 A | 8/1995 | Biedermann et al. | |
| 5,466,237 A | 11/1995 | Byrd, III et al. | |
| 5,466,238 A * | 11/1995 | Lin | 606/264 |
| 5,474,551 A | 12/1995 | Finn et al. | |
| 5,474,555 A | 12/1995 | Puno et al. | |
| 5,476,464 A | 12/1995 | Metz-Stavenhagen et al. | |
| 5,480,401 A | 1/1996 | Navas | |
| 5,480,440 A | 1/1996 | Kambin | |
| 5,499,983 A * | 3/1996 | Hughes | 606/61 |
| 5,501,684 A | 3/1996 | Schlapfer et al. | |
| 5,520,690 A | 5/1996 | Errico et al. | |
| 5,531,746 A | 7/1996 | Errico et al. | |
| 5,549,608 A | 8/1996 | Errico et al. | |
| 5,554,157 A | 9/1996 | Errico et al. | |
| 5,575,792 A | 11/1996 | Errico et al. | |
| 5,578,033 A | 11/1996 | Errico et al. | |
| 5,584,834 A | 12/1996 | Errico et al. | |
| 5,586,984 A | 12/1996 | Errico et al. | |
| 5,591,166 A | 1/1997 | Bernhardt et al. | |
| 5,607,426 A | 3/1997 | Ralph et al. | |
| 5,609,593 A | 3/1997 | Errico et al. | |
| 5,647,873 A | 7/1997 | Errico et al. | |
| 5,649,926 A | 7/1997 | Howland et al. | |
| 5,669,911 A | 9/1997 | Errico et al. | |
| 5,672,176 A | 9/1997 | Biedermann et al. | |
| 5,733,285 A | 3/1998 | Errico et al. | |
| 5,733,286 A | 3/1998 | Errico et al. | |
| 5,817,094 A | 10/1998 | Errico et al. | |
| 5,876,403 A * | 3/1999 | Shitoto | 606/61 |
| 5,882,350 A | 3/1999 | Ralph et al. | |
| 5,885,286 A | 3/1999 | Sherman et al. | |
| 5,951,553 A | 9/1999 | Betz et al. | |
| 5,964,761 A | 10/1999 | Kambin | |
| 5,964,988 A | 10/1999 | LaRose et al. | |
| 6,022,350 A | 2/2000 | Ganem | |
| 6,030,389 A | 2/2000 | Wagner et al. | |
| 6,053,917 A | 4/2000 | Sherman et al. | |
| 6,063,090 A | 5/2000 | Schlapfer | |
| 6,074,391 A | 6/2000 | Metz-Stavenhagen et al. | |
| 6,077,262 A | 6/2000 | Schlapfer et al. | |
| 6,090,110 A | 7/2000 | Metz-Stavenhagen | |
| 6,090,111 A | 7/2000 | Nichols | |
| 6,113,601 A | 9/2000 | Tatar | |
| 6,231,575 B1 * | 5/2001 | Krag | 606/264 |
| 6,280,442 B1 | 8/2001 | Barker et al. | |
| 6,296,644 B1 * | 10/2001 | Saurat et al. | 606/61 |
| 6,315,779 B1 | 11/2001 | Morrison et al. | |
| 6,585,738 B1 | 7/2003 | Mangione et al. | |
| 6,682,530 B2 | 1/2004 | Dixon et al. | |
| 6,736,817 B2 | 5/2004 | Troxell et al. | |
| 6,755,829 B1 | 6/2004 | Bono et al. | |
| 6,858,031 B2 | 2/2005 | Morrison et al. | |
| 6,884,241 B2 | 4/2005 | Bertranou et al. | |
| 6,887,241 B1 | 5/2005 | McBride et al. | |
| 7,220,262 B1 * | 5/2007 | Hynes | 606/61 |
| 7,322,979 B2 * | 1/2008 | Crandall et al. | 606/256 |
| 2002/0007183 A1 | 1/2002 | Lee et al. | |
| 2002/0026194 A1 | 2/2002 | Morrison et al. | |
| 2002/0143332 A1 * | 10/2002 | Lin et al. | 606/61 |
| 2003/0032957 A1 | 2/2003 | McKinley et al. | |
| 2003/0105460 A1 | 6/2003 | Crandall et al. | |
| 2003/0114853 A1 | 6/2003 | Burgess et al. | |
| 2003/0135210 A1 | 7/2003 | Dixon et al. | |
| 2004/0054371 A1 * | 3/2004 | Dierks et al. | 606/73 |
| 2004/0087949 A1 | 5/2004 | Bono et al. | |
| 2004/0092931 A1 | 5/2004 | Taylor et al. | |
| 2004/0127897 A1 | 7/2004 | Freid et al. | |
| 2004/0225290 A1 | 11/2004 | Ferree | |
| 2005/0038434 A1 | 2/2005 | Mathews | |
| 2005/0049588 A1 | 3/2005 | Jackson | |
| 2005/0113927 A1 * | 5/2005 | Malek | 623/17.16 |
| 2005/0215999 A1 | 9/2005 | Birkmeyer et al. | |
| 2005/0234451 A1 | 10/2005 | Markworth | |
| 2005/0234452 A1 | 10/2005 | Malandain | |
| 2005/0234456 A1 | 10/2005 | Malandain | |
| 2006/0149252 A1 | 7/2006 | Markworth et al. | |

FOREIGN PATENT DOCUMENTS

| | | |
|---|---|---|
| DE | 94 02 695.5 (U1) | 5/1994 |
| FR | 2 780 631 | 1/2000 |
| WO | 00/54681 | 9/2000 |
| WO | 02/076315 | 10/2002 |
| WO | 2004/064603 | 8/2004 |
| WO | 2004/093701 | 11/2004 |

* cited by examiner

SCREW WITH DEPLOYABLE INTERLACED DUAL RODS

TECHNICAL FIELD

This invention relates to medical devices.

BACKGROUND

The use of spinal stabilization/fixation devices to align or position specific vertebra or a region of the spine is well established. Typically such devices utilize a spinal fixation element, comprised of a relatively rigid member such as a plate, board or rod that is used as a coupler between adjacent vertebrae. Such a spinal fixation element can effect a rigid positioning of adjacent vertebrae when attached (e.g. to the pedicle portion of the vertebra) using bone anchorage screws (e.g. pedicle screws). Once the coupled vertebrae are spatially fixed in position, procedures can be performed, healing can proceed or spinal fusion may take place.

Spinal fixation elements may be introduced posteriorly to stabilize the various vertebrae of the spine, for example, in conjunction with a kyphoplasty procedure wherein a void or cavity is made inside a vertebral body followed by filling with a bone substitute to form an "internal cast." Some conventional devices for this purpose are designed to be attached directly to the posterior of the spine, but the generally invasive nature of a conventional posterior approach used to implant these devices poses drawbacks. One minimally invasive solution to the problem of the posterior approach involves making a longitudinal separation of the sacrospinalis group between the multifudus and longissimus utilizing the natural cleavage plane between these two muscles rather than detaching the paraspinal muscles from the posterior spinal elements. Problems stemming from the prior art solutions include a high degree of invasiveness resulting in muscle disruption and blood loss. The loss of the paraspinal muscle attachment sites, formation of scar tissue, and loss of muscle function may compromise the patient's final outcome. Additionally, the prior art solutions are time consuming and are difficult to remove.

SUMMARY

In general, in one aspect, the invention features a medical device for supporting a structure including a screw assembly. The screw assembly includes a base, one or more arms, and an interconnection means for coupling the base to the one or more arms. The interconnection means allows the one or more arms to be positionable in a first position that is substantially parallel to a long axis of the base, and secondarily positionable substantially perpendicular to the long axis of the base. The base is configured for attachment to a structure in a patient and the one or more arms are configured for attachment to one or more support structures.

Implementations of the invention can include one or more of the following features. The structure in a patient can be bone. The screw assembly can have an overall length sized for subcutaneous support of the posterior of a spine. The base of the screw assembly can include a base head and an anchor.

The interconnection means of the screw assembly can include the base head of the screw assembly, and the base head can include a receiver and a setscrew. In one implementation, the setscrew secures the base to the one or more arms of the screw assembly. In another implementation, tightening the setscrew effects locking of the one or more arms in a position in relation to the base of the screw assembly. In one implementation, the interconnection means includes the base head of the screw assembly and the base head includes a hinge means.

The one or more arms of the device can include a body, wherein the body has an elongate shape and includes a connector end for attachment to a support structure, and a receiver end for connection to the base head receiver portion of the interconnection means. In one implementation, the elongate shape of the arm body can include an offset section, wherein the offset section is configured to provide a linear alignment of the base and the arm body when the arm is positioned substantially parallel to a long axis of the base. In another implementation, the elongate shape of the arm body is a shape configured for fitted interrelation between two or more arms positioned in a first position that is substantially parallel to a long axis of the base. In another implementation, the receiver end of the one or more arms and the receiver portion of the base head include a hinge means. In another implementation, a means is provided for locking the arm into a position substantially perpendicular to the long axis of the base. In one implementation, the means provided for locking the arm can include a one-way ratchet, a setscrew or a cam.

Implementations of the invention can include one or more of the following features. The screw assembly of the device can include two arms and the receiver ends of the two arms can be configured for interconnection. In one implementation, one of the receiver ends of the two arms includes a first collet-type receiver end having a substantially cylindrical recess, and the other receiver end of the two arms includes a substantially cylindrical shape for interconnection with the first collet-type receiver. In another implementation, one of the receiver ends of the two arms can include a first collet-type receiver end having a substantially spherical recess, and the other receiver end of the two arms can include a substantially spherical shape for interconnection with the first collet-type receiver.

In one implementation, the invention can include following feature. The one or more support structures of the device can include an anchor, an aperture configured for attachment of an arm of the screw assembly, and a locking means configured to lock the arm of the screw assembly to the support structure.

In another implementation, the invention can include the following feature. The interconnection means of the screw assembly can include a hinge, a pin or a collet.

In general, in another aspect, the invention features a method of supporting the spine, the method comprising the steps of: 1) delivering to bone a screw assembly having one or more arms, a base and an interconnections means; 2) delivery to flanking bone one or more support structures having an aperture and locking means for the arms of the screw assemblies; 3) deploying the one or more arms of the screw assembly to the flanking support structures; 4) locking the one or more arms of the screw assembly in a desired position; and 5) engaging the locking means of the support structure aperture.

Aspects of the invention may include one of the following advantageous features. In various implementations of the invention the offset section of the arm body can be configured to provide a low-profile to the screw assembly when the one or more arms are positioned substantially parallel to a long axis of the base. The low profile is advantageous since it facilitates placement of the screw assembly and arms of the device as a single unit, in a minimally invasive manner, through for example, a narrow access channel, port or cannula.

The details of one or more embodiments of the invention are set forth in the accompanying drawings and the descrip-

DESCRIPTION OF DRAWINGS

Like reference symbols in the various drawings indicate like elements.

DETAILED DESCRIPTION

Figure 1A:
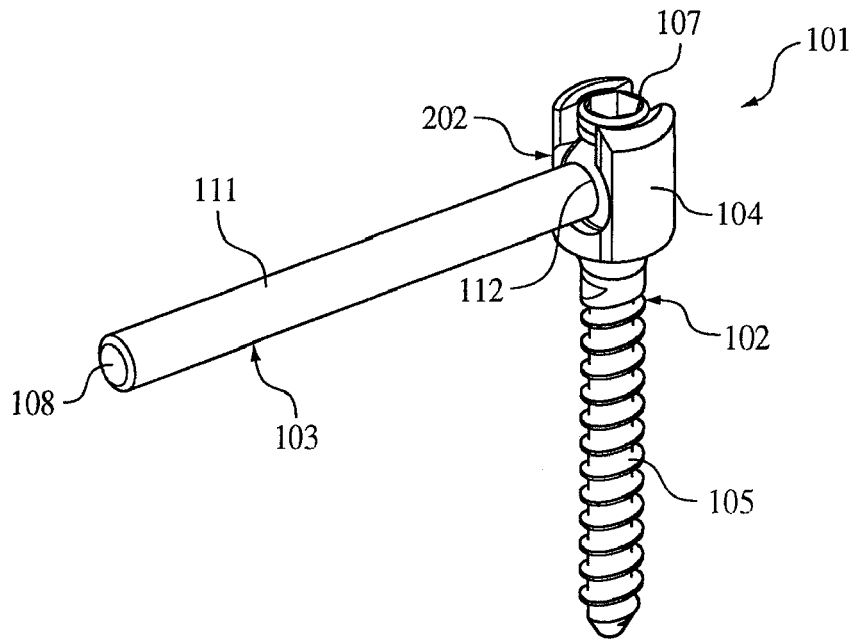
FIGS. 1A-1C are drawings of a screw assembly.

As shown in FIGS. 1A-1C and 1E, a screw assembly 101 is provided including a base 102 and one or more arms 103 in a single unit. The arm 103 and base 102 of the screw assembly 101 are coupled by an interconnection means. The base 102 of the screw assembly 101 is configured for attachment to a structure (e.g., a bone) and the arm 103 is configured for attachment to a support structure (described in detail below). In application, a screw assembly 101 having one or more arms 103 is attached to one or more support structures to form a support assembly 301 (see FIGS. 3A and 3B). The support assembly 301 can be used for temporary or permanent implantation.

Figure 1B:
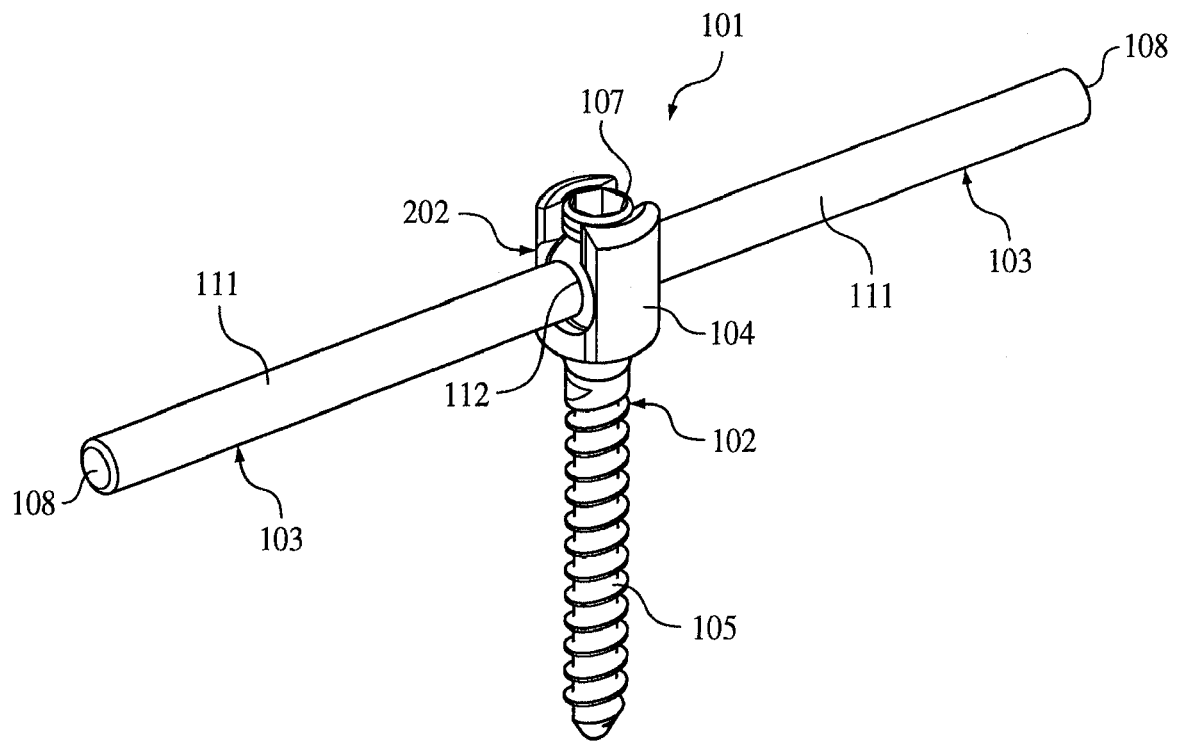

As shown in FIGS. 1A and 1B, the screw assembly 101 interconnection means can facilitate free-rotational (or multiaxial) movement of an arm 103 in relation to the base 102. The interconnection means can be selected from any number of means including but not limited to: a hinge means, a collet means, and a pin. As shown in FIGS. 1A and 1B, the interconnection means comprises a receiver end 112 disposed within a receiver 202 of a base 102. In this implementation, the arm 103 can have a substantially spherical-shaped receiver end 112 connected to a complementary-shaped receiver 202 in the base head 104. Additionally, the base head 104 can be closed or open (e.g. open-saddle as shown in FIG. 1A). The free-rotational arm 103 movement facilitated by the interconnection means is substantially a cone-shaped range of movement having an axis about which such movement is centered ("cone axis" hereinafter).

In use, the implementation as shown in FIGS. 1A and 1B can be used to provide support to a structure in a patient (e.g. a spine having a series of vertebrae). Where the structure supported is a spine, and the spine includes a long axis ("spinal axis" hereinafter), the screw assembly 101 can provide support to the spine substantially collinearly with the spinal axis. Specifically, the cone axis of movement of the arm 103 of the screw assembly 101 can optionally be disposed so that the cone axis is substantially collinear with the spinal axis. This arrangement provides a degree of adjustability when positioning the arm 103 and base 102 of the screw assembly 101 in relation to the structure being supported (e.g. a series of vertebrae). For example, where three sequential vertebrae are to be supported by a support assembly 301 including a screw assembly 101 having two arms 103 and two support structures (described in detail below), the three points of attachment to the three vertebrae can be substantially linear. Alternatively, the three points of attachment are not necessarily substantially linear.

Figure 1C:
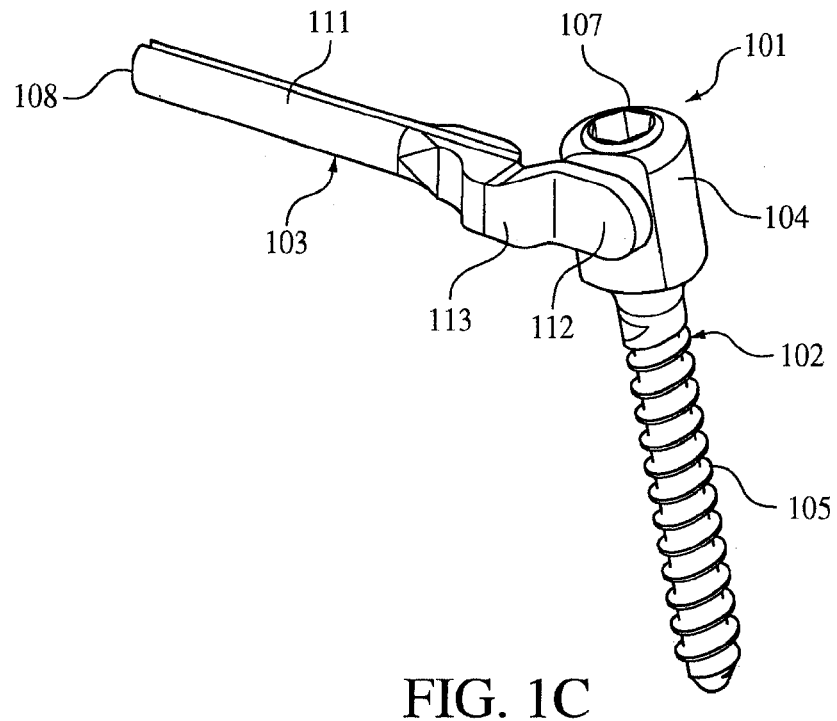
Figure 1D:
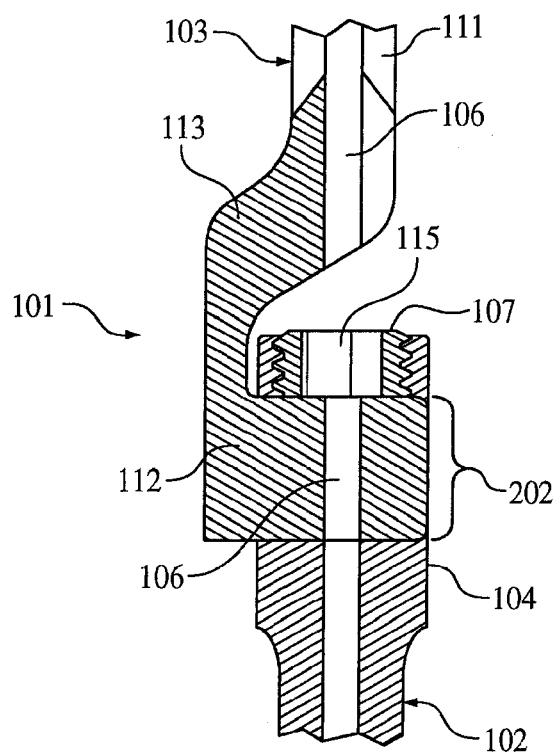
FIG. 1D is a cross-sectional drawing of a screw assembly.
Figure 1E:
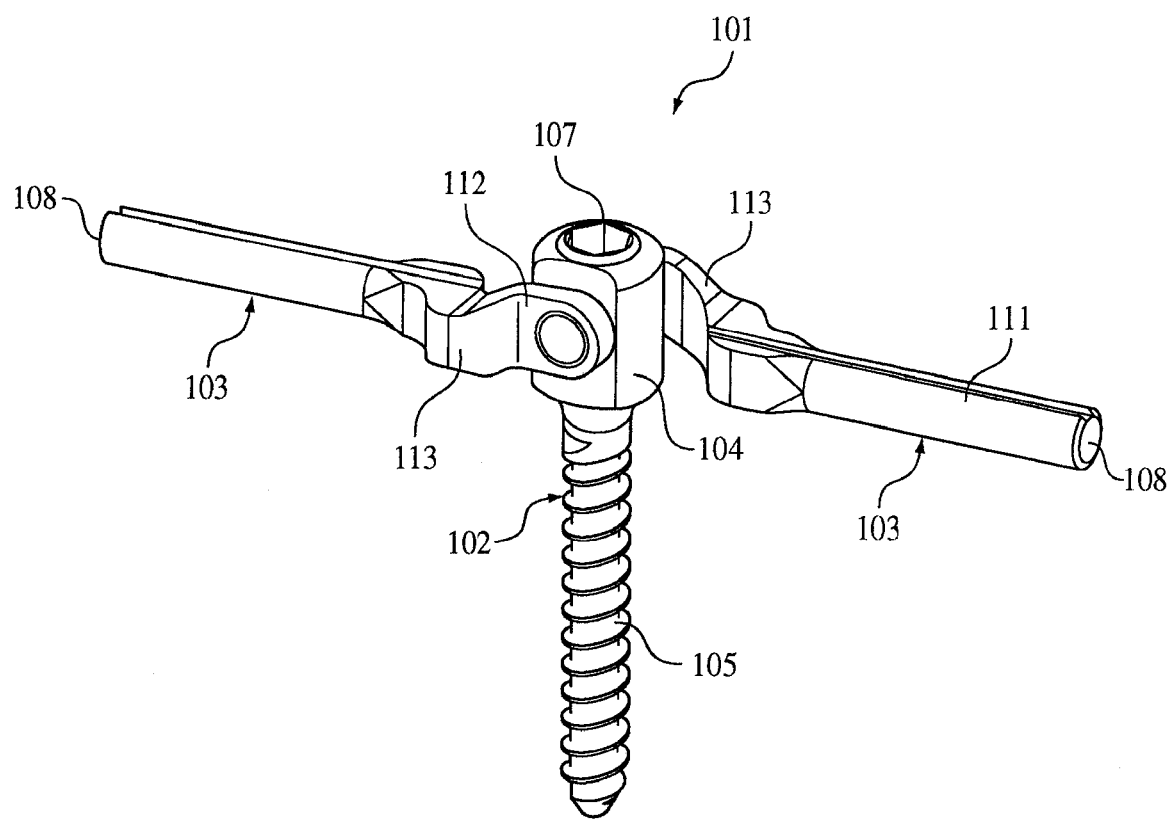
FIG. 1E is a drawing of a screw assembly.
Figure 2A:
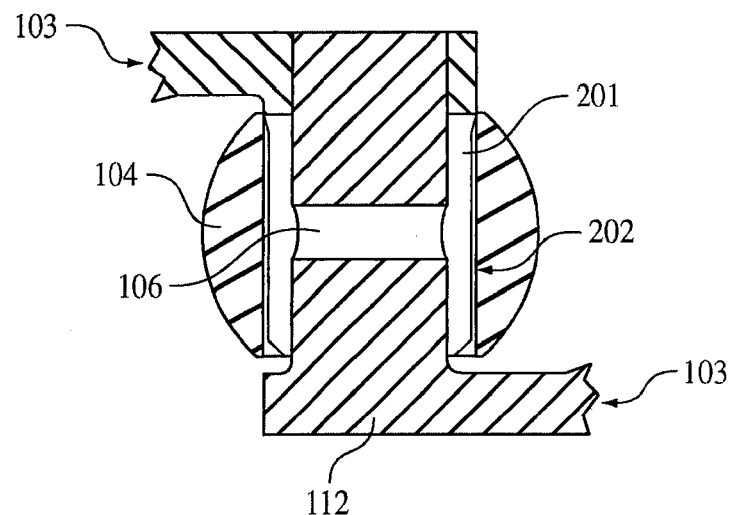
FIGS. 2A and 2B are cross-sectional drawings of a screw assembly.

In another implementation, as shown in FIGS. 1C and 1E, the interconnection means comprises one or more receiver end(s) 112 of one or more arm(s) 103 disposed within a base head 104 of a base 102. In this implementation the interconnection means can facilitate movement between the arm 103 and the base 102, such that the arm 103 is positionable in a first position that is parallel to a long axis of the base 102 (shown in FIGS. 1D, 2B, and 2D) and positionable in a second position that is perpendicular to the long axis of the base 102 (shown in FIGS. 1C and 1E). Additionally, the screw assembly 101 interconnection means can facilitate free-rotational (or multiaxial) movement of an arm 103 in relation to the base 102. As discussed above, the free-rotational movement of the arm 103 can be substantially a cone-shaped range of movement having a cone axis. In use, the implementation as shown in FIGS. 1C and 1E can be used to provide support to a structure in a patient (e.g. a spine having a series of vertebrae). As discussed for the implementation described above and shown in FIGS. 1A and 1B, the present implementation can provide support to the spine substantially collinearly with the spinal axis. Optionally, as shown in FIGS. 2C and 2D, an implementation wherein support is provided substantially collinearly with the spinal axis can include a cone axis of movement of the arm 103 of the screw assembly 101 disposed so that the cone axis is substantially perpendicular with the spinal axis. This arrangement provides a similar degree of arm 103 adjustability and advantages as discussed above for the implementation shown in FIGS. 1C and 1E.

The screw assembly 101 can be made of materials that are durable and that can be implanted in a body, including titanium, stainless steel, carbon fiber, etc. In one implementation, the screw assembly 101 is made of titanium. In another implementation the screw assembly 101 is made of a biocompatible material, a reabsorbable material, or a combination of any of the foregoing materials. The dimensions of the screw assembly 101 vary with the application. In general, in implementations as shown in FIGS. 1C and 1E, wherein the arm 103 is positionable in a first position that is substantially parallel to the long axis of the base 102, the length of the screw assembly 101 is from substantially 20 to 1,000 millimeters. In one implementation, the length is substantially between 50 and 400 millimeters. In another implementation, the screw assembly 101 is sized for applications involving support of multiples levels of the posterior of the spine (see FIG. 4). In another implementation, as shown in FIGS. 1A and 1B, the length of the base 102 is from substantially 20 to 100 millimeters and the length of the one or more arms 103 is from substantially 20 to 600 millimeters. In another implementation the length of the base 102 and the length of the arm 103 are each from substantially between 20 and 600 millimeters. In another implementation, the combined length of the base 102 and the arm 103 is sized for applications involving support of multiple levels of the posterior of the spine (see FIG. 4).

Figure 2B:
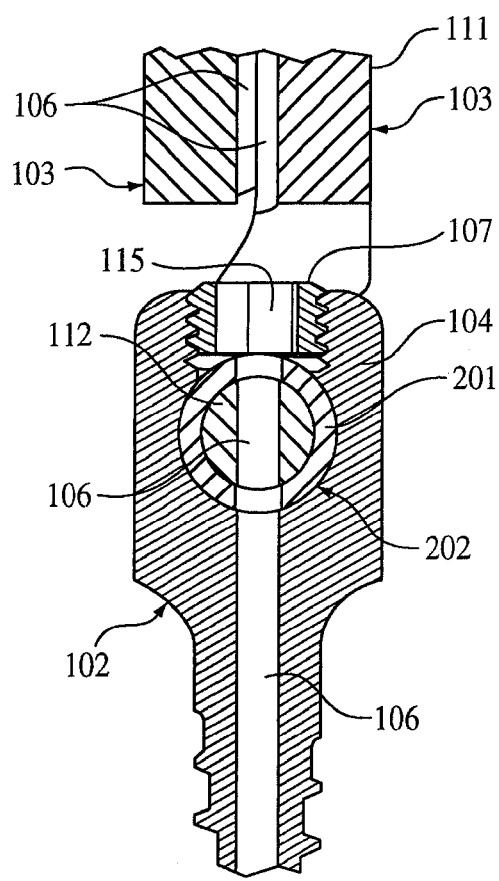
Figure 2C:
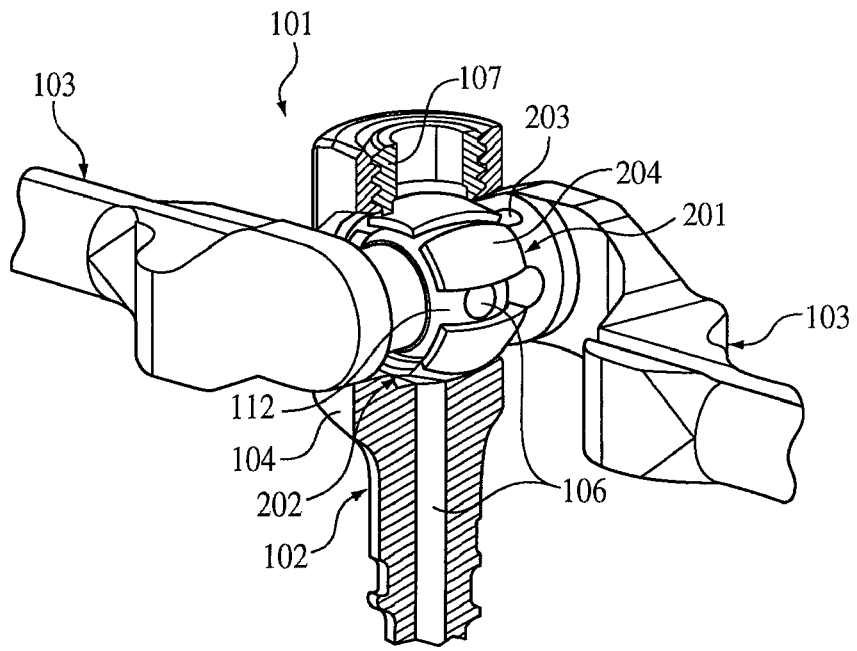
FIG. 2C is a drawing of a screw assembly showing a spherical-shaped collet-type connection between two arms and a cross-sectional view of a base.
Figure 2D:
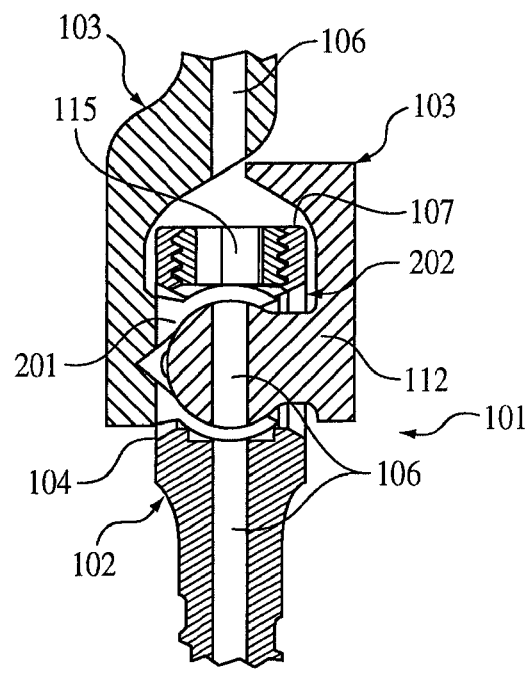
FIG. 2D is a cross-sectional drawing of a screw assembly showing a spherical-shaped collet-type connection between two arms.

In one implementation, as shown in FIGS. 1D, 2B, and 2D, the screw assembly 101 includes a longitudinal aperture 106. The longitudinal aperture 106 traverses the length of the screw assembly 101, and provides an aperture for the passage of instruments, tools, and guides (e.g. a K-wire) when the arm 103 is positioned in a first position that is parallel to a long axis of the base 102 (see FIGS. 1D, 2B, and 2D).

As shown in FIGS. 1A-1C and 1E, the base 102 of the screw assembly 101 is comprised of a base head 104 and an anchor 105. The anchor 105 can be a screw, staple, hook, or nail, and can be of a type typically used for bone anchoring. In one implementation the anchor 105 is a screw of a type for insertion into a pedicle of a vertebra (see FIGS. 1A-1C, 1E, 3A-3B and 4).

In one implementation, as shown in FIGS. 2A-2D, the interconnection means for coupling the base to the arms is comprised of the base head 104. The base head 104 can include a receiver 202 for receiving the receiver ends 112 of the screw assembly arms 103. In another implementation, the base head 104 is configured for hinged attachment of one or more screw assembly arms 103 using a hinge means (not shown). Such a means for connecting the base head 104 and the one or more screw assembly arms 103 is disclosed in U.S. application Ser. No. 10/825,962, filed Apr. 16, 2004, which is incorporated herein by reference in its entirety.

The base head 104 can include a locking means. As shown in FIGS. 1A-1D and 2B-2D, the locking means can be a setscrew 107. The base head 104 can be designed to include an open-saddle (see FIGS. 1A and 1B) or closed configuration (see FIGS. 1C-1E) for accommodating the locking means (e.g. a setscrew 107). In one implementation, the locking means is a setscrew 107, which secures the base 102 and the one or more arms 103 of the screw assembly 101 together.

In use, a screw assembly 101 including a base 102, one or more arms 103 and a locking means can be pre-assembled for delivery to a structure. Alternatively, the screw assembly 101 can be delivered as separate pieces for assembly at the site of a structure.

As shown in FIGS. 1A, 1B, 1D and 2B-2D, tightening the setscrew 107 can effect locking of one or more arms 103 into a position in relation to the base 102. In an implementation as shown in FIGS. 1D and 2B-2D, after one or more arms 103 of a screw assembly 101 are deployed from a first position that is substantially parallel to a long axis of the base to a second position that is substantially perpendicular to the long axis of the base 102, the setscrew 107 can be tightened to effect locking of the one or more arms 103 in the second position. In an alternative implementation, a cam (not shown) can be substituted for the setscrew 107.

In another implementation, as shown in FIG. 1A, wherein a single arm 103 is connected to the base 102, the setscrew 107 can be tightened to effect locking of the arm 103 into a position. In this implementation, the arm 103 can have a substantially spherical-shaped receiver end 112 connected to a complementary-shaped receiver 202 in the base head 104. The base head 104 can be closed or open (e.g. open-saddle as shown in FIG. 1A). Tightening the setscrew 107 can create a load that compresses the receiver end 112 of the arm 103 against the receiver 202 to effect locking of the arm 103 into a position. As shown in FIG. 2C, the receiver 202 can be a substantially spherical collet-type receiver. In such an implementation, tightening the setscrew 107 creates a load that compresses the receiver end 201 of the arm 103 against the receiver 202, thereby deflecting one or more deformable fingers 204 around the receiver end 112 to effect locking of the arm 103 into a position (see FIG. 2C).

In another implementation, as shown in FIG. 1B, wherein two arms 103 are connected to the base 102, the setscrew 107 can be tightened to effect locking of both arms 103 into a position. In this implementation, a first arm 103 can include a substantially spherical collet-type receiver end 201 and the second arm can include a receiver end 112 configured to interconnect within the receiver end 201 (see FIGS. 2C and 2D). As shown in FIG. 2C, tightening the setscrew 107 can create a load that compresses the receiver end 201 of the first arm 103 against the receiver end 112 of the second arm 103, thereby deflecting one or more deformable fingers 204 of the receiver end 201 around the receiver end 112 of the second arm 103 to effect simultaneous locking of both arms 103 into a position.

The receiver end 201 of the first arm 103 and the receiver end 112 of the second arm 103 can also be configured to provide for step-wise locking of each arm 103 into a position in relation to the base head 104. For example, the receiver end 201 of the first arm can be configured such that initial tightening creates a load that compresses the receiver end 112 against the base head receiver 202 to effect locking of the first arm 103 into a position without affecting the free rotational movement of the second arm 103. Upon final tightening, the increased load created thereby can compresses the receiver end 201 of the first arm 103 against the receiver end 112 of the second arm 103, thereby deflecting one or more deformable fingers 204 of the receiver end 201 around the receiver end 112 of the second arm 103 to effect locking of the second arm 103 into a position.

In another implementation, as shown in FIG. 1D, the setscrew 107 can be tightened to effect locking of a single arm 103 having a cylindrical shaped receiver end 112, by creating a load that compresses the receiver end 112 of the arm 103 against the complementary-shaped receiver 202.

In yet another implementation, as shown in FIG. 2B, the setscrew 107 can be tightened to effect locking of two arms 103, wherein the first arm 103 includes a substantially cylindrical collet-type receiver end 201 and the second arm 103 (not shown) includes a receiver end 112 configured to interconnect within the collet-type receiver end 201. In this implementation, tightening the setscrew 107 creates a load that compresses the substantially cylindrical collet-type receiver end 201 of the first arm 103 against the receiver 202 (see FIG. 2B), thereby deflecting one or more deformable fingers 204 (not shown) around the receiver end 112 of the second arm 103 to effect locking of both arms 103 into a position.

In a further implementation, as shown in FIGS. 2C and 2D, the setscrew 107 can be tightened to effect locking of two arms 103, wherein the first arm 103 includes a substantially spherical collet-type receiver end 201 and the second arm 103 includes a receiver end 112 configured to interconnect within the collet-type receiver end 201. In this implementation, tightening the setscrew 107 creates a load that compresses the substantially spherical collet-type receiver end 201 of the first arm 103 against the receiver 202, thereby deflecting one or more deformable fingers 204 around the receiver end 112 of the second arm 103 to effect locking of both arms 103 into a position (see FIG. 2C).

In another implementation, shown in FIGS. 1D, 2B and 2D, the setscrew 107 includes a setscrew aperture 115. The setscrew aperture 115 can be configured to substantially align with the longitudinal aperture 106 of the base 102, thereby enabling through passage between the longitudinal aperture 106 of the arm 103 and base 102 (as discussed above).

As shown in FIGS. 1A-1D, and 3A-3B, the one or more arms 103 of the screw assembly 101, include a body 111 wherein the body 111 has an elongate shape and includes a connector end 108 for attachment to a support structure 109, and a receiver end 112. In one implementation, the elongate shape of the body 111 of the arm 103 is a rod. In another implementation, the elongate shape of the body 111 of the arm 103 is substantially a longitudinally split rod. In another implementation, the elongate shape of the body 111 of the arm 103 is a shape configured for fitted interrelation between two or more arms 103 positioned in a first position that is substantially parallel to a long axis of the base 102 (not shown). For example, the fitted interrelation can be comprised of a longitudinally split rod shape.

In another implementation, as shown in FIGS. 1C-1E and 3A-3B, the elongate shape of the body 111 of the arm 103 includes an offset section 113. The offset section 113 can be configured to provide a low-profile to the screw assembly 101 when the one or more arms 103 are positioned substantially parallel to a long axis of the base 102 (See FIGS. 1D and 2B). Additionally, the offset section 113 can provide a linear alignment of the base 102 and the body 111 of the arm 103 when the arm 103 is positioned substantially parallel to a long axis of the base 102 (See FIGS. 1D and 2B).

In another implementation, as shown in FIGS. 1D, 2B and 2D, the body 111 of the arm 103 includes a longitudinal aperture 106. In one implementation, the longitudinal aperture 106 is a channel or groove running the length of the body 111 of the arm 103 (not shown). In a further implementation, two interrelating arms 103 can have longitudinal apertures 106 that align to form a single longitudinal aperture 106 when the arms 103 are interrelated. The longitudinal aperture 106 of the body 111 of the arm 103 can be coaxially aligned with the longitudinal aperture 106 of the base 102 of the screw assembly 101. The longitudinal aperture 106 traverses the length of the screw assembly 101, and provides an aperture for the passage of instruments, tools, and guides (e.g. a K-wire)

The receiver ends 112 of the one or more arms 103 can include a hinge means for hinged interconnection with the base head 104 (not shown). In such an implementation, a locking means can be provided whereby after deployment, the one or more arms 103 are lockable into a position substantially perpendicular to the long axis of the base 103. An example of such a locking means can be a one-way ratchet configuration (not shown).

In another implementation, the receiver end 112 of a single arm 103 can be cylindrical shape for interconnection within the receiver 202 of the base head 104. In such an implementation the receiver 202 can be an aperture in which the receiver end 112 of the arm 103 is received.

In another implementation, the receiver ends 112 of two arms 103 can be interconnecting and disposed within the base head 104. For example, the receiver ends 112 can interconnect by way of a collet-type design. In a first example, the two interconnecting receiver ends 112 can have a cylindrical-shaped collet-type design including: a first collet-type receiver end 201 having a substantially cylindrical recess, one or more relief cuts 203 and one or more deformable fingers 204, and; a second solid cylindrical-shaped receiver end 112 configured for fitting into the cylindrical recess of the collet-type receiver end 201 (not shown).

In a second example, as shown in FIGS. 1A, 1B, 2C and 2D, the two interconnecting receiver ends 112 can have a spherical-shaped collet-type design including: a first collet-type receiver end 201 having a substantially spherical recess, one or more relief cuts 203 and one or more deformable fingers 204, and; a second solid spherical-shaped receiver end 112 configured for fitting into the first collet-type receiver end 201.

Additionally, as shown in FIGS. 2A and 2B, which illustrate a cylindrical shaped collet-type design, and FIGS. 2C and 2D, which illustrate a spherical-shaped collet-type design, the respective receiver ends 112 can include a longitudinal aperture 106 passing through the interconnected receiver ends 112. Such a longitudinal aperture 106 can be configured to provide coaxial alignment with the longitudinal aperture 106 of the base 102, when the arms 103 are positioned substantially parallel to the long axis of the base 102 (see FIGS. 2B and 2D).

Figure 3A:
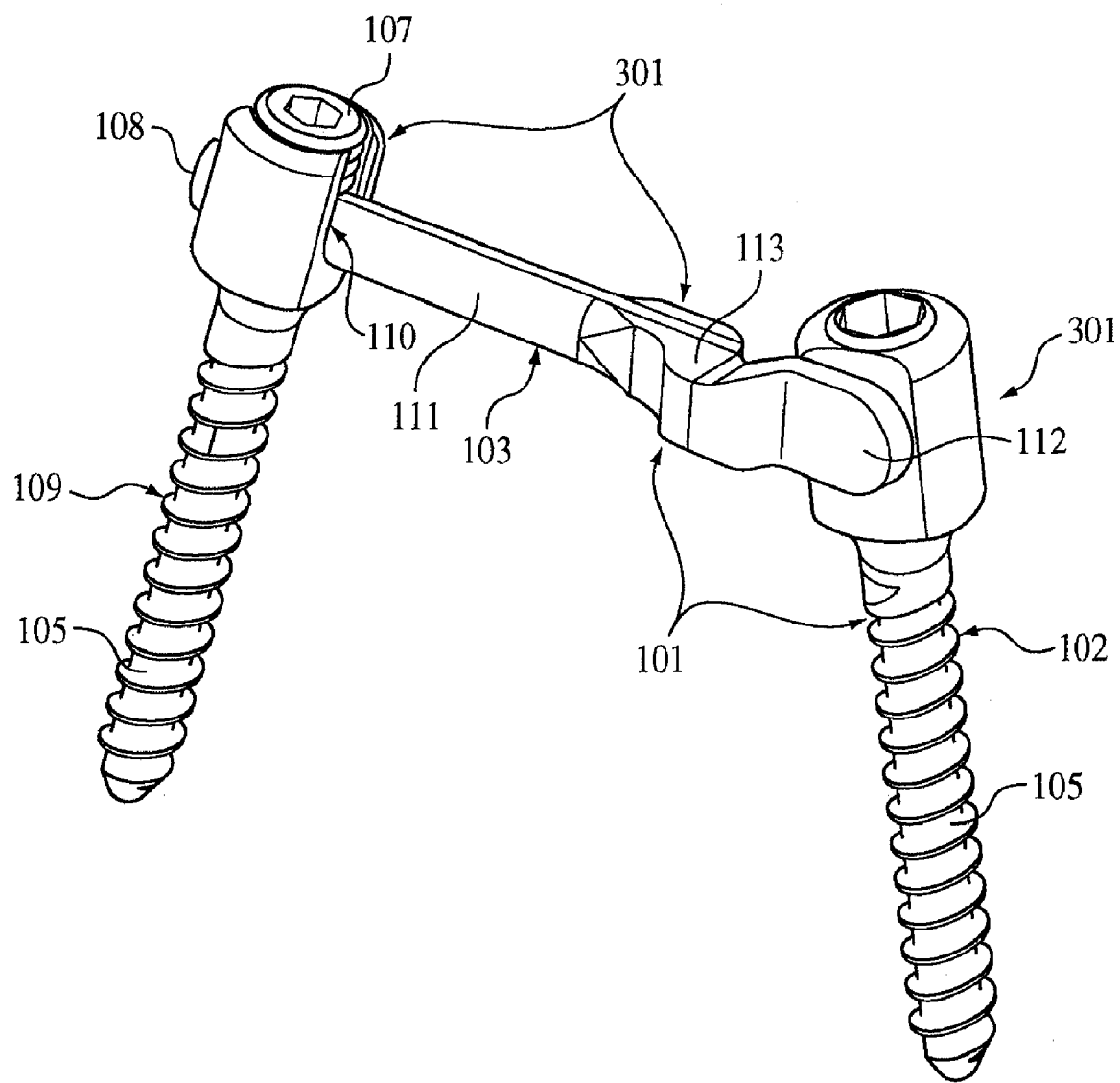
FIG. 3A is a drawing of a support assembly showing a screw assembly having one arm and a base attached to a support structure.
Figure 3B:
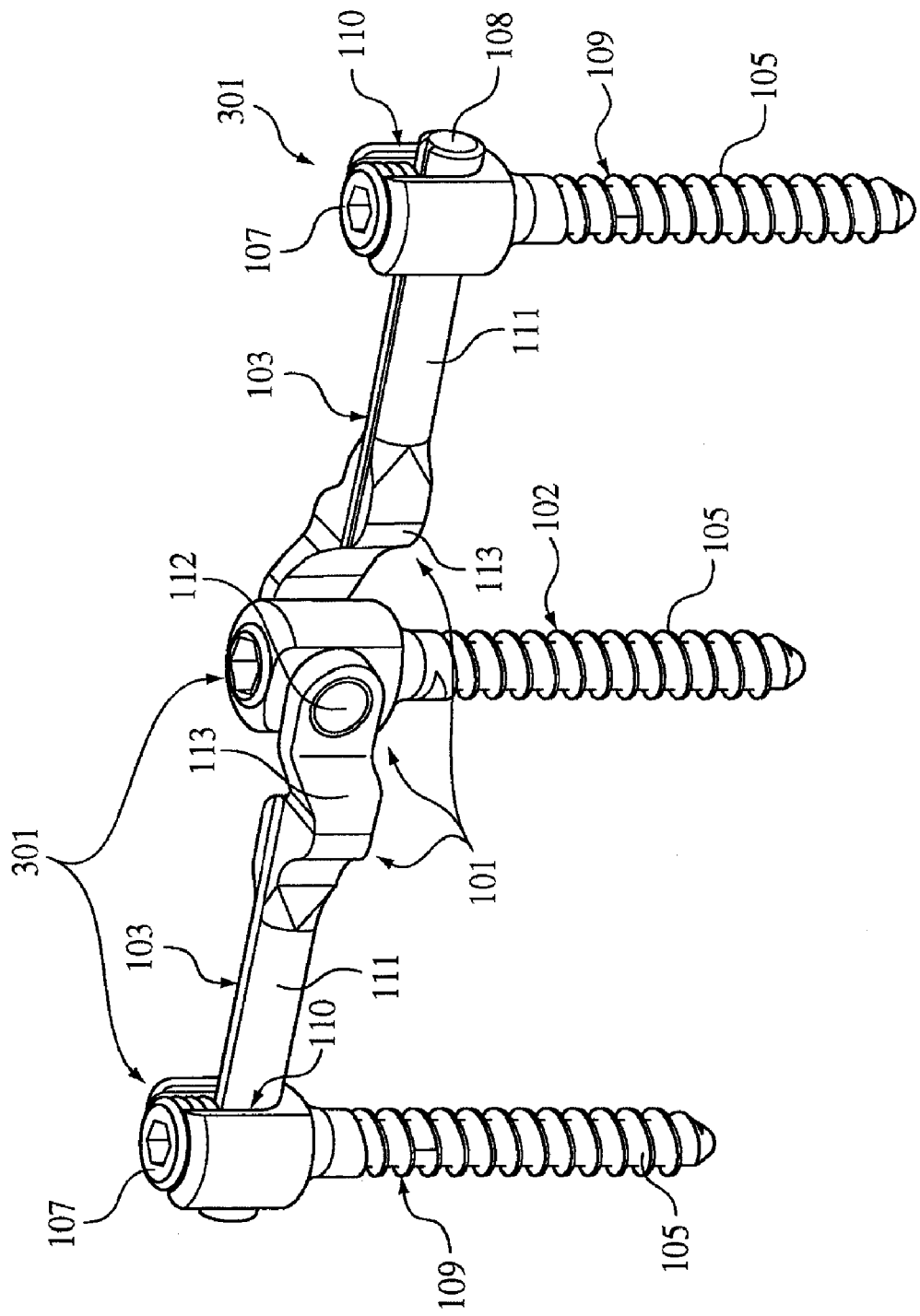
FIG. 3B is a drawing of a support assembly showing a screw assembly having two arms and a base attached to two support structures.

As shown in FIGS. 1A-1D, 3A and 3B, the connector ends 108 of the one or more arms 103 are configured for attachment to a support structure 109. As shown in FIGS. 3A and 3B, one or more support structures 109 can be attached to a screw assembly 101 to provide a support assembly 301. In one implementation, each support structure 109 is comprised of an anchor 105, an aperture 110, and a locking means (see FIGS. 3A and 3B). The one or more support structures 109 can be made of materials that are durable and that can be implanted in a body, including titanium, stainless steel, carbon fiber, etc. In one implementation, the one or more support structures 109 are made of titanium. In another implementation the one or more support structures 109 are made of a biocompatible material, a reabsorbable material, or a combination of any of the foregoing materials.

In one implementation, each support structure 109 is configured for attachment to a structure in a patient (e.g. bone). As shown in FIGS. 3A and 3B, the locking means for the one or more support structures 109 can be a setscrew 107. Alternatively, the locking means can be a cam (not shown).

Figure 4:
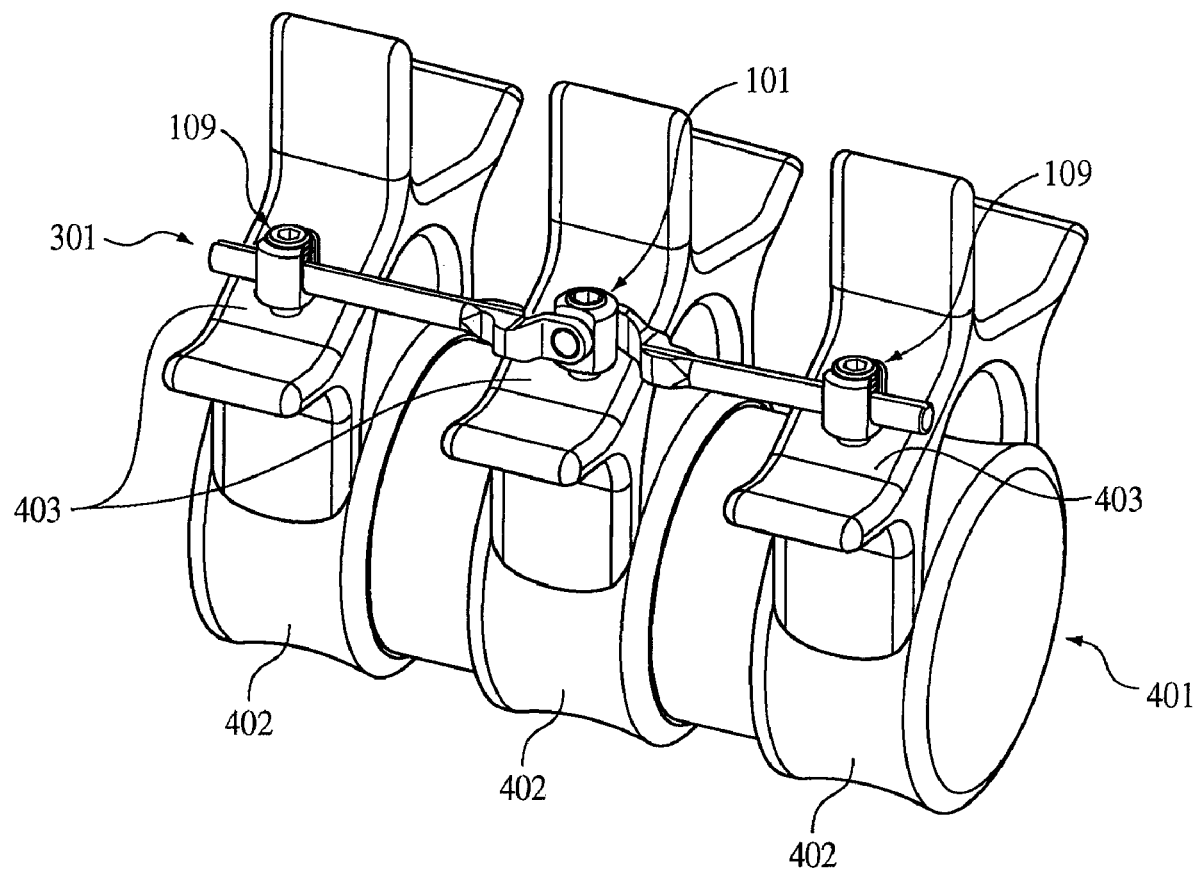
FIG. 4 is a drawing showing a support assembly implanted into the pedicles of the vertebrae of a spine.

As shown in FIG. 4, two support structures 109 can be attached to a screw assembly 101 to provide a support assembly 301 that can be implanted into the pedicles 403 of vertebra 402 in a spine 401 to effect support of the spine 401. In another implementation, a single support structure 109 can be attached to a screw assembly 101 to provide a support assembly 301 that can be implanted into the pedicles 403 of vertebra 402 in a spine 401 to effect support of the spine 401.

Referring to FIGS. 3A, 3B and 4, a method of using the invention to support the spine 401 includes the steps of: 1) delivering to bone a screw assembly 101 having one or more arms 103, a base 102 and an interconnection means (e.g. a base head receiver 202 interconnected with the receiver end 112 of one or more arms 103); 2) delivering to flanking bone, one or more support structures 109 having apertures 110 and locking means for the connector ends 108 of the arms 103 of the screw assemblies 101; 3) deploying the one or more arms 103 of the screw assembly 101 to the flanking support structures 109; 4) locking the one or more arms 103 of the screw assembly 101 in a desired position; and 5) engaging the locking means of the support structure 109 apertures 110. In one implementation, the one or more flanking support structures 109 can be delivered, for example, to bone including one or more vertebral bodies on one or both sides of a vertebral body to which the screw assembly 101 is delivered. In another implementation, the one or more flanking support structures 109 are delivered to vertebral bodies adjacent to the vertebral body to which the screw assembly 101 is delivered. In another implementation, one or more of the flanking support structures 109 are delivered to vertebral bodies distal to the adjacent-most vertebral body.

The method of supporting the spine can also be used in conjunction with a kyphoplasty procedure. Kyphoplasty is a percutaneous technique involving the use of an expandable structure, such as a balloon catheter, to create a cavity or void within the vertebral body, followed by filling the cavity with a bone substitute to form an "internal cast". The bone substitute could be any appropriate filling materials used in orthopedic surgery, including but not limited to, allograft or autograft tissue, hydroxyapatite, epoxy, PMMA bone cement or synthetic bone substitutes, medical grade plaster of Paris or calcium phosphate or calcium sulfate cements. Methods and instruments suitable for such treatment are more fully described in U.S. Pat. Nos. 4,969,888 and 5,108,404, which are incorporated herein by reference. Kyphoplasty can be used to reduce vertebral compression fractures and to move bone with precision, thus restoring as close to normal the pre-fracture anatomy of the vertebral body. Vertebral compression fractures caused by trauma (for example, due to automobile accidents or falls) have traditionally been treated with open reduction, internal fixation stabilization hardware and fusion techniques using a posterior approach. The stabilization hardware is used to offload the fractured vertebral body and to stop motion across the disk so that bone graft can fuse one vertebral body to the next and the stabilization hardware usually becomes a permanent implant. In trauma, the stabilization hardware may be designed to facilitate easy removal after fusion has occurred. Stabilization hardware can take many forms, including those described herein.

The combination of kyphoplasty and insertion of stabilization hardware utilizing the naturally occurring interior muscle plane as described in Wiltse and Spencer, Spine (1988) 13(6):696-706, satisfies the goals of improving the quality of patient care through minimally invasive surgical therapy.

A number of preferred embodiments of the invention have been described. Nevertheless, it will be understood that various modifications may be made without departing from the spirit and scope of the invention. For example, while the some implementations have been described using screws to anchor into bony structures, the scope of the invention is not so limited. Any means of anchoring can be used, such as a cam, screw, staple, nail, pin, or hook. Accordingly, other embodiments are within the scope of the following claims.

What is claimed is:

1. A medical device for supporting one or more bones comprising:
 a screw assembly including:
  a screw having an anchor configured for insertion into bone, a base head, and a base coupled between the anchor and the base head, where the base head includes a receiver defining an aperture opening at opposite sides of the receiver and the aperture further opening at a proximal end of the receiver and a locking device in engagement with the receiver in the proximal end opening of the aperture, and
  one or more arms extending along a longitudinal axis, said one or more arms include an offset section extending through one of the side openings of the aperture of the receiver with the offset section rotatably attached to the base head, the offset section extending to a body so that the one or more arms are rotatable from a first position where the body and the longitudinal axis are substantially co-axially aligned with a long axis of the base to a second position where the body and the longitudinal axis are substantially perpendicular to the long axis of the basis while the offset section extends from the base head in offset relation to the long axis and the longitudinal axis, wherein the locking device is movable into the receiver through the proximal end opening of the aperture to contact the offset section in the receiver of the base head,
 where each arm of the one or more arms is configured to directly connect to a support structure having an anchor at a first end configured for insertion into bone.

2. The medical device of claim 1, wherein the screw assembly has an overall length sized for subcutaneous support of the posterior of a spine.

3. The medical device of claim 1, wherein the locking device is a setscrew configured to fix a position of the one or more arms relative to the base head.

4. The medical device of claim 1, where the base head includes a hinge configured to allow an arm of the one or more arms to move relative to the base head.

5. The medical device of claim 1, wherein each of the one or more arms comprises:
 a body having an elongate shape and including:
  a connector end configured to attach the body to the support structure, and
  a receiver end configured to join with the receiver of the base head.

6. The medical device of claim 5, wherein the elongate shape of the arm body includes the offset section configured to provide a linear alignment of the base and the arm body when the arm is positioned substantially parallel to the long axis of the base.

7. The medical device of claim 5, wherein the elongate shape of the arm body is configured for fitted interrelation between two or more arms positioned in a first position that is substantially parallel to the long axis of the base.

8. The medical device of claim 5, wherein the receiver end of the one or more arms and the receiver of the base head are rotatably attached using a hinge.

9. The medical device of claim 8, wherein the position of each of the one or more arms is fixable in the second position substantially perpendicular to the long axis of the base.

10. The medical device of claim 9, wherein the one or more arms are fixably positioned using one or more of a one-way ratchet, a setscrew, or a cam.

11. The medical device of claim 5, wherein the screw assembly includes two arms and the receiver ends of the two arms are interconnected with one another within the receiver of the base head.

12. The medical device of claim 11, wherein a first arm of the two arms includes a first collet-type receiver end having a substantially cylindrical recess, and a second arm of the two arms includes a cylindrical shaped receiver end where the receiver end of the first arm is configured to interconnect with the receiver end of the second arm, wherein tightening of the locking device in the receiver compresses the receiver end of the first arm against the receiver end of the second arm to simultaneously lock the first and second arms into position.

13. The medical device of claim 11, wherein a first arm of the two arms includes a first collet-type receiver end having a substantially spherical recess, and a second arm of the two arms includes a substantially spherical shaped receiver end where the receiver end of the first arm is configured to interconnect with the receiver end of the second arm, wherein tightening of the locking device in the receiver compresses the receiver end of the first arm against the receiver end of the second arm to simultaneously lock the first and second arms into position.

14. The medical device of claim 5, where the screw includes a first longitudinal aperture and the arm body includes a second longitudinal aperture such that when the arm is positioned substantially parallel to the long axis of the base, the first and second apertures are substantially aligned and traverse an entire length of the screw assembly through the screw and the arm body.

15. The medical device of claim 1, wherein the support structure further comprises:

an aperture located at a second end and configured to fixably attach an arm of the screw assembly to the support structure.

16. The medical device of claim 1, wherein one or more of the arms are rotatably attached to the base head using one or more of a hinge, a pin, or a collet.

17. A method of supporting the spine, the method comprising:
attaching a screw assembly to a bone, the screw assembly having one or more arms and a screw having an anchor configured for insertion into bone, a base head and a base coupled between the base head and the anchor, where the base head includes a receiver defining an aperture opening at opposite sides of the receiver and the aperture further opening at a proximal end of the receiver and a locking device in engagement with the receiver through the proximal end opening of the aperture, where the one or more arms extend along a longitudinal axis and are configured to include an offset section extending through one of the side openings of the aperture of the receiver with the offset section rotatably attached to the base head and extending to a body so that the one or more arms are rotatable from a first position where the body and the longitudinal axis are substantially coaxially aligned with a long axis of the base to a second position where the body and the longitudinal axis are substantially perpendicular to the long axis of the basis while the offset section extends from the base head in offset relation to the long axis and the longitudinal axis, wherein the locking device is movable into the receiver through the proximal end opening of the aperture to contact the offset section in the receiver of the base head;
attaching one or more support structures to adjacent bones, each support structure having an anchor at a first end configured for insertion into bone and an aperture at a second end configured to receive an arm of the one or more arms;
deploying the one or more arms of the screw assembly to one or more respective support structure apertures;
fixing the one or more arms of the screw assembly in a desired position; and
securing each of the one or more arms to the respective support structures.

18. A system comprising:
a screw assembly, including:
a screw having an anchor configured for insertion into bone, a base head, and a base coupled between the anchor and the base head, where the base head includes a receiver defining an aperture opening at opposite sides of the receiver and the aperture further opening at a proximal end of the receiver and a locking device engaged to the receiver in the proximal end opening of the aperture, and
one or more arms extending along a longitudinal axis, said one or more arms include an offset section extending through one of the side openings of the aperture of the receiver with the offset section rotatably attached to the base head, the offset section extending to a body so that the one or more arms are rotatable from a first position where the body and the longitudinal axis are coaxially aligned with a long axis of the base to a second position where the body and the longitudinal axis are substantially perpendicular to the long axis of the basis while the offset section extends from the base head in offset relation to the long axis and the longitudinal axis, wherein the locking device is movable into the receiver through the proximal end opening of the aperture to contact the offset section in the receiver of the base head where each arm of the one or more arms is configured to directly connect to a support structure; and
one or more support structures including:
an anchor at a first end configured for insertion into bone, and
an aperture at a second end for receiving a respective arm of the one or more arms.

19. A medical device for supporting one or more bones comprising:
a screw assembly including:
a screw having an anchor configured for insertion into bone, a base head, and a base coupled between the anchor and the base head, and
two arms rotatably attached to the base head so that the two arms are interconnected with one another within the base head and are rotatable from a first position substantially parallel to a long axis of the base to a second position where each arm extends from the base head in opposite directions from one another and substantially perpendicular to the long axis of the basis while the two arms are attached to the base head, where each arm is configured for attachment to a respective support structure.

20. The medical device of claim 19, further comprising:
two support structures including;
an anchor at a first end configured for insertion into bone, and
an aperture at a second end for receiving a respective arm of the two arms included in the screw assembly.

* * * * *